US006248909B1

(12) United States Patent
Akimoto et al.

(10) Patent No.: US 6,248,909 B1
(45) Date of Patent: Jun. 19, 2001

(54) TRIGLYCERIDE AND COMPOSITION COMPRISING THE SAME

(75) Inventors: Kengo Akimoto, Mishima-gun; Toshiaki Yaguchi, Ibaraki; Shigeaki Fujikawa, Takatsuki, all of (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/335,730

(22) Filed: Jun. 18, 1999

(30) Foreign Application Priority Data

Jun. 19, 1998 (JP) .................................................. 10-173017

(51) Int. Cl.⁷ .................................................. C07C 57/00
(52) U.S. Cl. .............................. 554/1; 514/547; 426/601; 426/648; 426/807
(58) Field of Search ........................... 554/227; 514/547; 426/601, 648, 807

(56) References Cited

FOREIGN PATENT DOCUMENTS

| 0 120 169 | 10/1984 | (EP) . |
|---|---|---|
| 265699 * | 5/1988 | (EP) . |
| 0 265 699 | 5/1988 | (EP) . |
| 5-87497 | 10/1984 | (JP) . |
| 4-12920 | 4/1988 | (JP) . |
| 6-70786 | 3/1994 | (JP) . |
| 6-287594 | 10/1994 | (JP) . |
| 7-107904 | 4/1995 | (JP) . |

OTHER PUBLICATIONS

Miyashita et al., Chem. abstr., vol. 113, No. 17, abstract 147859, 1990*
Endo et al., JAOCS, vol. 74, No. 9, pp. 1041–1045, 1997.*
Daubert et al., JAOCS, vol. 66, No. 9, pp. 1507–1509, 1944*
Lyapkov et al., Chem. abstr., vol. 109, abstract 127483, 1988.*
K. Miyashita et al., Chemical Abstracts, 113(17):336, Abstract No. 113 (Oct. 22, 1990).
J.J. Myher et al., *Lipds*, 31(2):207–215 (1996).
W.W. Christie, *Analysis of Oils and Fats*, Chapter 7, "The Positional Distributions of Fatty Acids in Triglycerides", pp. 313–339 (1986).
C.I. Lanting et al., *The Lancet*, 344:1319–1322 (1994).
Y. Endo et al., *J. AM. Oil Chem. Soc.*, 74(9):1041–1045 (Sep. 1997).
B.F. Daubert et al., *Journal of the American Chemical Society*, 66(9):1507–1509 (1944).
S. Carlson et al., *Proc. Natl. Acad. Sci USA*, 90:1073–1077 (1993).
S. Carlson et al., *Advances in Polyunsaturated Fatty Acid Research*, pp. 261–264 (1993).
S. Innis et al., *Lipids*, 31(5):497–505 (1996).
S. Aoe et al., *J. Nutr.*, 127:1269–1273 (Jul. 1997).
J.W. Liu et al., *J. Am. Oil Chem. Soc.*, 75(4):507–510 (Apr. 1998).

* cited by examiner

*Primary Examiner*—Deborah D. Carr
(74) *Attorney, Agent, or Firm*—Burns, Doane, Swecker & Mathis, L.L.P.

(57) ABSTRACT

The present invention provides a novel triglyceride and a composition containing that novel triglyceride having a triglyceride structure of the human breast milk type, which triglyceride has a saturated fatty acid having 16–18 carbon atoms at the position 2, at the position 1 and/or 3; which is and at least one ω6, ω9 or ω3 unsaturated fatty acid manufactured by subjecting a glyceride in which a saturated fatty acid having 16 to 18 carbon atoms is bonded at position 2 to transesterification using a lipase and a ω6, ω9 or ω3-unsaturated fatty acid.

22 Claims, No Drawings

TRIGLYCERIDE AND COMPOSITION COMPRISING THE SAME

This application claims priority under 35 U.S.C. §§119 and/or 365 to 10-173017 filed in Japan on Jun. 19, 1998; the entire content of which is hereby incorporated by reference.

BACKGROUND OF THE INVENTION

1. Field of Invention

The present invention relates to a novel triglyceride and a composition comprising the same, and more particularly, to a triglyceride having a saturated fatty acid having 16 to 18 carbon atoms at the position 2 of the triglyceride, and having a ω6, ω9 and/or (3 unsaturated fatty acids at the positions 1 and/or 3.

2. Related Art

The majority of the lipids that so far obtained are neutral fats that comprise a mixture of triglycerides in which various fatty acids are randomly ester-bonded to the positions 1, 2 and 3 of the triglyceride. These lipids were shown to demonstrate different absorption properties and physiological activities according to differences in the bonding positions of the fatty acids. Lipids in which specific fatty acids are bonded to predetermined positions of triglyceride (structured lipids) have recently attracted considerable attention.

For example, Japanese Examined Patent Publication No. 4-12920 discloses a triglyceride having satisfactory digestion and absorption property in which a fatty acid having 8 to 14 carbon atoms is bonded to the position 2 of the triglyceride and fatty acids having 18 or more carbon atoms are bonded to the positions 1 and 3. In addition, since it is known that 2-monoglycerides are of a form that is most easily absorbed by the human body, Japanese Examined Patent Publication No. 5-87497 discloses a triglyceride in which a 0)3 or 0)6 highly unsaturated fatty acid having physiological function is bonded to the position 2, while saturated fatty acids easily hydrolyzable by enzymes of the digestive tract are bonded at the positions 1 and 3. However, there is no disclosure or suggestion of the relationship between the physiological properties and the structure of triglycerides in human breast milk having unsaturated fatty acids.

On the other hand, with respect to the physiological function of fatty acids, attention has focused in recent years on arachidonic acid and docosahexaenoic acid. These fatty acids are contained in human breast milk and have been reported to be useful in infant development (Advances in Polyunsaturated Fatty Acid Research, Elsevier Science Publishers, 1993, pp. 261–264) and to be important in infant growth and brain development (Proc. Natl. Acad. Sci. USA, 90, 1073–1077 (1993), Lancet, 344, 1319–1322 (1994)).

Several official agencies have recommended intake values (premature infants: arachidonic acid: 60 mg/kg, docosahexaenoic acid: 40 mg/kg; normal infants: arachidonic acid: 20 mg/kg, docosahexaenoic acid: 20 mg/kg body weight/day (WHO-FAO (1994)). In several countries in Europe, premature infant formulas have been marketed that contain docosahexaenoic acid and arachidonic acid produced by fermentation blended as triglycerides. However, there have been no considerations given to the bonding positions of arachidonic acid and/or docosahexaenoic acid in the triglycerides added to these formulas.

The triglyceride structure in human breast milk is predicted to be such that there is a high proportion of triglycerides in which palmitic acid (16:0) is bonded to position 2 of the triglyceride, and a high proportion of triglycerides in which highly unsaturated fatty acid or medium chain fatty acid is bonded to positions 1 and 3 (Christie, W. W. (1986): The Positional Distribution of Fatty Acids in Triglycerides, Analysis of Oils and Fats, Hamilton, R. J. and Russell, J. B. eds., pp. 313–339, Elsevier Applied Science, London). However, these are merely suppositions based on the results of analysis of fatty acids in triglycerides, while isolation and structural analysis of triglycerides in human breast milk have not yet been attempted.

In addition, although triglycerides containing arachidonic acid produced by fermentation have been added to formula to allow fatty acid composition to more closely approximate the composition of human breast milk as previously described, since the structure of these triglycerides containing arachidonic acid is such that there is a high proportion of triglycerides in which palmitic acid and other saturated fatty acids are bonded at the positions 1 and 3 while unsaturated fatty acids are bonded at position 2 (J. J. Myher, A. Kuksis, K. Geher, P. W. Park and D. A. Diersen-Schade, Lipids, 31, pp. 207–215 (1996)), it is different from the structure of triglycerides hypothesized in human breast milk.

Thus, there is a strong desire to develop lipids surmised to have the glyceride structure of human breast milk, and more specifically, triglycerides reliably confirmed to have a structure in which saturated fatty acid having 16 to 18 carbon atoms is bonded at the position 2 of the triglyceride, while highly unsaturated fatty acids or medium chain fatty acids are bonded at positions 1 and 3.

SUMMARY OF THE INVENTION

Thus, the object of the present invention is to provide a novel triglyceride having at the position 2 a saturated fatty acid of 16 to 18 carbon atoms, and at the positions 1 and 3 unsaturated fatty acids wherein at least one of these unsaturated fatty acids is a ω6, ω9 or ω3 unsaturated fatty acid; or a novel triglyceride having at position 2 a saturated fatty acid of 16 to 18 carbon atoms, having at one of positions 1 and 3 a saturated fatty acid of 4 to 18 carbon atoms, and having at another position of the positions 1 and 3 a ω6, ω9 or ω3 unsaturated fatty acid; and a composition containing this novel triglyceride.

As a result of earnest research to solve the above-mentioned problems, the inventors of the present invention found that triglyceride estimated to be of target human breast milk type can be manufactured starting from a glyceride clearly determined to have a saturated fatty acid of 16 to 18 carbon atoms at the position 2, allowing lipase that specifically acts on ester bonds at the positions 1 and 3 to act on said glyceride in the presence of ω6, ω9 or ω3 unsaturated fatty acid or ester thereof, resulting in transesterification only at the positions 1 and 3, so as to obtain a triglyceride having at the position 1 and/or 3 ω6, ω9 or ω3 unsaturated fatty acids. Moreover, by comparing the resulting triglyceride with triglyceride obtained from human breast milk, the present inventors also determined for the first time that triglyceride having a saturated fatty acid of 16 to 18 carbon atoms at the position 2 of the triglyceride and highly unsaturated fatty acids at the positions 1 and 3 is in fact present in human breast milk, thereby leading to completion of the present invention.

DETAILED DESCRIPTION

The present invention relates to a novel triglyceride, as well as a food composition, animal feed, therapeutic nutritional product and pharmaceutical composition comprising said triglyceride.

According to the present invention, there is provided a triglyceride represented with the following general formula (I):

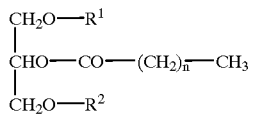

(I)

wherein $R^1$ and $R^2$ are acyl groups of unsaturated fatty acids having 18 to 22 carbon atoms, these acyl groups may be oxidized, and n represents an integer of 14 to 16, and at least one of $R^1$ or $R^2$ is a ω6, ω9 or ω3 unsaturated fatty acid; or, a triglyceride represented with the following general formula (II):

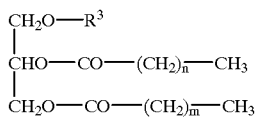

(II)

wherein, $R^3$ represents an acyl group of an ω6, ω9 or ω3-unsaturated fatty acid having 18 to 22 carbon atoms, this acyl group may be oxidized, n represents an integer of 14 to 16, and m represents an integer of 2 to 16.

The fatty acid that is present at the positions 1 and/or 3 of the triglyceride of the present invention is ω3, ω6 and/or ω9 unsaturated fatty acid. More specifically, examples of the ω3 unsaturated fatty acids include:
9,12,15-octadecatrienoic acid (α-linolenic acid) [18:3, ω3];
6,9,12,15-octadecatetraenoic acid (stearidonic acid) [18:4, ω3];
11,14,17-eicosatrienoic acid (dihomo-α-linolenic acid) [20:3, ω3];
8,11,14,17-eicosatetraenoic acid [20:4, ω3], 5,8,11,14,17-eicosapentaenoic acid [20:5, ω3];
7,10,13,16,19-docosapentaenoic acid [22:5, ω3]; and
4,7,10,13,16,19-docosahexaenoic acid [22:6, ω3].

In addition, examples of the ω6 unsaturated fatty acids include:
9,12-octadecadienoic acid (linoleic acid) [18:2, ω6];
6,9,12-octadecatrienoic acid (γ-linolenic acid) [18:3, ω6];
8,11,14-eicosatrienoic acid (dihomo-γ-linolenic acid) [20:3 ω6];
5,8,11,14-eicosatetraenoic acid (arachidonic acid) [20:4, ω6];
7,10,13,16-docosatetraenoic acid [22:4, ω6] and
4,7,10,13,16-docosapentaenoic acid [22:5, ω6].

Moreover, examples of the ω9 unsaturated fatty acids include:
6,9-octadecadienoic acid [18:2, ω9];
8,11-eicosadienoic acid [20:2, ω9]; and
5,8,11-eicosatrienoic acid (Mead acid) [20:3, ω9].

Moreover, acyl residues may be hydroxylated, epoxidated or hydroxyepoxidated acyl residues.

The fatty acid that is present at the position 2 of the novel triglyceride of the present invention is a fatty acid having 16 to 18 carbon atoms, examples of which include palmitic acid (16:0) and stearic acid (18:0).

Representative triglycerides of the present invention include:

1,3-diarachidonyl-2-palmitoyl triglyceride,
1-arachidonyl-3-docosahexaenoyl-2-palmitoyl triglyceride,
1-arachidonyl-3-octanoyl-2-palmitoyl triglyceride,
1,3-didocosahexaenoyl-2-palmitoyl triglyceride,
1-(dihomo-γ-linolenyl)-3-docosahexaenoyl-2-palmitoyl triglyceride,
1-docosahexaenoyl-3-octanoyl-2-palmitoyl triglyceride,
1-arachidonyl-3-(dihomo-γ-linolenyl)-2-palmitoyl triglyceride,
1-(dihomo-γ-linolenyl)-3-octanoyl-2-palmitoyl triglyceride,
1,3-bis(dihomo-γ-linolenyl)-2-palmitoyl triglyceride,
1,3-bis(5,8,11-eicosatrienoyl)-2-palmitoyl triglyceride,
1-(5,8,11-eicosatrienoyl)-3-octanoyl-2-palmitoyl triglyceride,
1-arachidonyl-3-(5,8,11-eicosatrienoyl)-2-palmitoyl triglyceride, and
1-docosahexaenoyl-3-(5,8,11-eicosatrienoyl)-2-palmitoyl triglyceride.

The novel triglyceride of the present invention can be manufactured by allowing lipase that specifically acts on the ester bonds at the positions 1 and 3 of triglyceride to act on a triglyceride having a saturated fatty acid of 16 to 18 carbon atoms bonded at the position 2, resulting in transesterification with an ω6, ω9 or ω3-unsaturated fatty acid or ester thereof.

Although examples of triglyceride having a saturated fatty acid of 16 to 18 carbon atoms bonded at the position 2 include tripalmitin (in which palmitic acid (16:0) is bonded at the positions 1, 2 and 3) and tristearin (in which stearic acid (18:0) is bonded at the positions 1, 2 and 3), it is not necessary for all the ester-bonded fatty acids in the triglyceride to be the same. Any fatty acid or any combination of fatty acids having 4 to 18 carbon atoms may be bonded to positions 1 or 3 provided a saturated fatty acid having 16 to 18 carbon atoms is bonded at the position 2 of the triglyceride.

Since oil or fat having saturated fatty acids of 16 or more carbon atoms for their constituent fatty acids have a high melting point, it may be necessary to raise the reaction temperature. For example, in the case of using tripalmitin, although varying according to the composition of the reaction mixture, the reaction might have to be carried out at 50 to 70° C. However, such a high temperature could be cause inactivation of enzyme and denaturation of unsaturated fatty acid added for the transesterification. Therefore, it is preferred that starting oil or fat having at the positions 1 and/or 3 low-melting point fatty acids of 8 to 12 carbon atoms, oleic acid, linoleic acid etc. is used for transesterification and that the transesterification is carried out at a temperature of 45° C. or lower.

Triglyceride of the present invention having at the position 2 a saturated fatty acid of 16 to 18 carbon atoms can have at any of the positions 1 and 3 an ω6, ω9 or ω3-unsaturated fatty acid. A triglyceride having a ω6, ω9 or ω3-unsaturated fatty acid at only one of the position 1 and 3 can be converted to a corresponding triglyerade having same or different ω6, ω9 or ω3-unsaturated fatty acids at both of the positions 1 and 3.

For example, triglycerides having saturated fatty acid at the position 2 and unsaturated fatty acid at one of the positions 1 and 3 can be obtained by culturing the genus Crypthecodenium, Thraustochytrium, Schizochytrium, Ulkenia, Japonochytorium or Haliphthoros.

From said triglycerides, for example, 1,2-dipalmitoyl-3-docosahexaenoyl triglyceride can be isolated. When a 1 and 3-positions-specific lipase acts on said glyceride resulting in transesterification with a ω6, ω9 or ω3-unsaturated fatty acid or an ester thereof, the docosahexaenorate at the position 3 is not transesterified while only palmitate at the position 1 is transesterified to provide a triglyceride having a ω6, ω9 or ω3-unsaturated fatty acid at the position 1, palmitic acid at the position 2 and docosahexaenoic acid at the position 3. More particularity, if arachidonic acid is used as said unsaturated fatty acid to be transestirified, a triglyceride having arachidonic acid at the position 1, palmitic acid at the position 2 and docosahexaenoic acid at the position 3 is obtained.

In the present invention, lipase that specifically acts on the positions 1 and 3 of triglyceride can be used as catalyst. Although there are no particular limitations on this lipase, examples include lipase produced by a microorganism belonging to the genus Rhizopus, Rhizomucor, Mucor, Penicillium, Aspergillus, Humicola or Fusarium, as well as porcine pancreatic lipase. Commercially available products can also be used for said lipase.

Examples of commercially available lipase include lipase of *Rhizopus delemar* (Tanabe Pharmaceutical, Dalipase), lipase of *Rhizomucor miehei* (Novo Nordisk, Ribozyme IM), lipase of *Aspergillus niger* (Amano Pharmaceutical, Lipase A), lipase of *Humicola lanuginosa* (Novo Nordisk, Lipolase), lipase of *Mucor javanicus* (Amano Pharmaceutical, Lipase M) and lipase of *Fusarium heterosporum*. These lipases may be used in their native form, or in the form of lipase that has been immobilized Asto cellite, ion exchange resin or a ceramic carrier.

The amount of water added to the reaction system is extremely important. Transesterification does not proceed in the absolute absence of water, while if the amount of water is too much, hydrolysis occurs, the triglyceride recovery rate decreases, or spontaneous acyl group transfer occurs in a partially acylated glyceride resulting in transfer of the saturated fatty acid at the position 2 to the position 1 or 3. Thus, when using an immobilized enzyme that does not have bonded water, it is effective to first activate the enzyme using a substrate to which water has been added before carrying out the reaction, and then use a substrate to which water is not added during the reaction. In order to activate the enzyme in batch reactions, a substrate containing water at 0 to 1,000% (wt %) of the amount of added enzyme should be used to pretreat the enzyme, and in the case of activating by a column method, a water-saturated substrate should be allowed to continuously flow through the column.

For example, the amount of water in a batch reaction for activating lipase of *Rhizopus delemar* (Tanabe Pharmaceutical, Dalipase) immobilized on cellite or a ceramic carrier is 10 to 200% (wt %) of the amount of enzyme added. However, the amount of water required for activation of an enzyme for the transesterification reaction is greatly influenced by the type of enzyme used. For example, water is not substantially required if lipase of *Rhizomucor miehei* (Novo Nordisk, Lipozyme IM) is used, and rather, any excess water must be removed. Excess water should be removed by hydrolyzing a triglyceride that does not impair the primary reaction for the substrate.

The amount of lipase used in a batch reaction may be determined according to the reaction conditions. Although there are no particular limitations on the amount of lipase, 1 to 30% (wt %) of the reaction mixture is suitable when using, for example, lipase of *Rhizopus delemar* or lipase of *Rhizomucor miehei* immobilized on cellite or a ceramic carrier.

Transesterification in a batch reaction is performed according to the method described below. Namely, an ω6, ω9 or ω3 unsaturated fatty acid or an ester thereof is added to triglyceride having a saturated fatty acid of 16 to 18 carbon atoms bonded at the position 2. Examples of fatty acid esters that can be used include methyl esters, ethyl esters, propyl esters and butyl esters. The triglyceride/fatty acid or triglyceride/fatty acid ester ratio used as starting materials is suitably 1:0.5–20. A suitable amount of activated or dehydrated lipase that specifically acts on positions 1 and 3 (normally 5,000 to 50,000 U/g; 1 U of lipase is the amount of enzyme that releases 1 pol of fatty acid per minute using olive oil as substrate) is added to the substrate followed by carrying out transesterification for 2 to 100 hours at 20 to 72° C. while stirring or shaking.

The above-mentioned immobilized enzyme can be used repeatedly. Namely, the reaction can be continued by leaving the immobilized enzyme in a reaction vessel after reaction and replacing the reaction mixture with freshly prepared reaction mixture comprising substrate. In addition, for transesterification by a column method, a reaction mixture containing substrate can be allowed to flow continuously at the rate of 0.05 to 20 ml/hr per gram of enzyme.

In addition, the content of target triglyceride can be increased by performing transesterification repeatedly. Namely, lipase specifically acting on the positions 1 and 3 of triglyceride is allowed to act in the presence of an 0)6, 0)9 or 0)3 unsaturated fatty acid or an ester thereof to obtain a reaction mixture in which fatty acids at positions 1 and 3 are transesterified to provide ω6, ω9 and/or ω3 unsaturated fatty acids.

Next, triglyceride is purified from said reaction mixture according to a method to be described later, and transesterification is again performed with ω6, ω9 or ω3-unsaturated fatty acid or an ester using said purified triglyceride as starting material. The content of the target triglyceride can be dramatically increased by repeating this transesterification, and transesterification should preferably be repeated 2 to 5 times.

In transesterification using a conventional immobilized lipase, a fatty acid acyl group bonded at the position 2 of partially esterified glyceride formed by hydrolysis that occurs as a side reaction is transferred to another position. In the present invention, however, hydrolysis can be nearly completely suppressed and the amount of partially esterified glyceride formed is about 1%, thereby solving the problem of the prior art. In addition, if the water content contained in the substrate is no more than several thousand ppm, hydrolysis that occurs as a side reaction can be ignored, and precise control of the water content in the substrate is not necessary.

Moreover, in contrast a decrease of enzyme activity after several uses in reactions in organic solvent or reactions at 50° C. or above using an immobilized enzyme in a conventional process, inactivation of enzyme does not occur in a reaction system of the present invention wherein the reaction is carried out at 45° C. or lower, and does not use organic solvent, making it possible to use the enzyme more than 20 times in batch reactions, and for more than 100 days in column reactions.

Due to the use of a simple substrate in the present invention, triglycerides obtained from the reaction comprises a few molecules species. Therefore, the target triglyceride can easily be isolated by routine methods such as liquid chromatography, molecular distillation, downstream membrane fractionation or vacuum superfractionation or a combination thereof. The triglycerides manufactured in the present invention are triglycerides in which unsaturated fatty acid is bonded at the positions 1 and/or 3, and said triglycerides exist in a form of mixture with unreacted starting glcycerides, unreacted unsaturated fatty acid or ester thereof, and fatty acids or esters thereof released by transesterification from the positions 1 and/or 3 of the starting triglyceride formed.

Therefore, purification of the target triglyceride having unsaturated fatty acids bonded at the positions 1 and/or 3 and a saturated fatty acid of 16 to 18 carbon atoms bonded at the position 2 can be performed by alkaline deacidation, steam distillation, molecular distillation, downstream membrane fractionation, vacuum superfractionation, column chromatography, solvent extraction or membrane separation, or a combination thereof so as to remove the above-mentioned fatty acids released by the transesterification and unreacted unsaturated fatty acids.

Since a triglyceride obtained in the present invention having a palmitic acid moiety bonded at the position 2 and arachidonic acid and/or docosahexaenoic acid moieties at the positions 1 and 3 is considered to have the same structure of triglyceride as in human breast milk, it can be effectively used for premature infant formula, infant formula, milk supplement, or formula for pregnant or lactating women. Namely, a triglyceride of the present invention having palmitic acid at the position 2 and arachidonic acid and/or docosahexaenoic acid at the positions 1 and/or 3 may be added to the manufacturing process or finished product of a formula such as premature infant formula, infant formula or milk supplement, a formula so as to obtain products more closely approximates human breast milk.

The present invention provides not only triglycerides having the same $\omega 6$, $\omega 9$ or $\omega 3$-unsaturated fatty acids at the positions 1 and 3, which is the same structure as triglycerides in human breast milk and useful for a source of $\omega 6$, $\omega 9$ and $\omega 3$-unsaturated fatty acids, but also triglycerides having different $\omega 6$, $\omega 9$ or $\omega 3$-unsaturated fatty acid moieties at the positions 1 and 3, such as triglyceride having a $\omega 6$-unsaturated fatty acid such as arachidonic acid at the position 1 and a $\omega 3$-unsaturated fatty acid such as docosahexaenoic acid at the position 3, which is more useful as a source of unsaturated fatty acids because one triglyceride molecule provides two different unsaturated fatty acids.

In addition to formula for administration to premature infants and infants, other possible uses of the triglycerides of the present invention include addition to milk, soy bean milk and other dairy products as well as addition to products using oils or fats. Examples of products using oils or fats include natural foods such as meat, fish and nut oils and fats, Chinese food, noodles, soups and other foods to which oil or fat is added during preparation, Japanese deep-fried found, fried foods, deep-fried bean curd, fried rice, doughnuts, deep-fried confections and other foods that use oil or fat as a heating medium, butter, margarine, mayonnaise, salad dressing, chocolate, instant noodles, caramel, cookies, ice cream and other oily foods or foods to which fats or oils are added during processing, and sweet bean jam-filled breads and other foods on which oil or fat is sprayed or coated during final processing.

Other examples include bread, noodles, rice, confections, their processed foods and other agricultural foods, rice wine, medicinal rice wine and other fermented foods, sweetened rice wine, vinegar, soy sauce, fermented bean paste, salad dressing, yogurt, ham, bacon, sausage, mayonnaise and other livestock food products, pressed fish, deep-fried seafood, fish cake and other marine food products, and fruit juices, soft drinks, sports drinks, alcoholic beverages, tea and other beverages.

In addition, in the case of using as health foods or functional foods, although the form may be that of the drug forms indicated below or the foods or beverages indicated above, they may be also be in a processed form such as natural liquid foods, semi-digested nutritional foods, component nutrient foods or drinks, containing proteins (although proteins such as milk protein, soy bean protein and egg white albumin having balanced amino acids and a high nutritional value are commonly used as protein sources, their decomposition products, egg white oligopeptides, soy bean hydrolysates or mixtures of individual amino acids may also be used), sugars, lipids, trace elements, vitamins, emulsifiers, fragrances and so forth.

Foods and beverages of the present invention can be processed and manufactured according to ordinary manufacturing methods by adding a prescribed amount of triglyceride of the present invention. The amount of addition varies according to drug form, food form and physical properties. Although the amount added is preferably 0.01 to 50% in general, there are no particular limitations on this amount. In addition, in the case of ingestion as a health food or functional food, triglyceride of the present invention can be administered to patients in the form of a functional food prepared locally by adding a novel triglyceride of the present invention during preparation of hospital foods under the supervision of a nutritionist in accordance with the dietary regimen prescribed by a physician based on physiological function and titer of highly unsaturated fatty acids bonded at positions 1 and 3 of triglyceride of the present invention.

In the case of using the triglyceride of the present invention as a pharmaceutical, the form of administration may be of any form provided oral or parenteral administration is suitably performed, examples of such forms include injection solutions, transfusion solutions, powders, granules, tablets, capsules, enteric coated pills, lozenges, internal liquid preparations, suspensions, emulsions, syrups, external liquid preparations, poultices, nose drops, inhalants, ointments, lotions and suppositories. These can be used either alone or in combination according to symptoms.

Each of these preparations can be prepared by using a known assistant that can be normally used in the field of pharmaceutical preparation technology, including vehicles, binders, antiseptics, stabilizers, decomposing agents, lubricants and correctives, with the primary drug according to the objective in accordance with routine methods.

Although the dose varies according to the objective of administration, the fatty acids bonded at the positions 1 and 3 of the triglyceride (physiological activity, titer, etc.) and the status of the patient receiving administration (sex, age, body weight, etc.), the normal adult dose in the case of oral administration is 0.01 mg to 10 g, preferably 0.1 mg to 2 g, and more preferably 1 mg to 200 mg, per day as the total amount of structured lipid of the present invention, and in the case of parenteral administration, 0.001 mg to 1 g, preferably 0.01 mg to 200 mg, and more preferably 0.1 mg to 100 mg, per day as the total amount of structured lipid of the present invention, and these doses can be suitably adjusted within the above ranges.

Moreover, the triglyceride of the present invention may be a triglyceride that has not previously been isolated or synthesized, and can be used as an analytical standard substance.

EXAMPLES

The following provides a detailed explanation of the present invention through its examples.

Furthermore, fatty acids and triglycerides are indicated with the following abbreviations in the present examples for the sake of convenience. To begin with, the following are used for single letter abbreviations representing fatty acids:

8: caprylic acid, P: palmitic acid, A: arachidonic acid, M: Mead acid, D: docosahexaenoic acid. Next, triglycerides are described with three letters consisting of a single letter abbreviation representing the fatty acid bonded at the position 1, a single letter abbreviation representing the fatty acid bonded at the position 2, and a single letter abbreviation representing the fatty acid bonded at the position 3. Thus, the structure of triglycerides is described as shown in the following example: 8P8 (triglyceride having caprylic acid bonded at the position 1, palmitic acid bonded at the position 2, and caprylic acid bonded at the position 3).

Example 1

Using a 1:2 (wt/wt) substrate mixture of tripalmitin (PPP) and caprylic acid, a reaction mixture comprising 10.5 g of said substrate mixture and 1.2 g of *Rhizomucor miehei* immobilized lipase (Novo Nordisk, Lipozyme IM60) was placed in a screw-cap vial and incubated while shaking (140 times/minute) for 48 hours at 50° C. After reaction, the reaction mixture was replaced with a fresh substrate mixture while leaving only the immobilized enzyme, and the next reaction was carried out under the same conditions. The reaction was carried out for 4 cycles while repeatedly using the immobilized enzyme, and the respective reaction mixtures were collected.

70 ml of 0.5 N KOH (20% ethanol solution) was added to each reaction mixture (10.5 g) and after extracting the glyceride fraction with 100 ml of hexane, the solvent was removed with an evaporator and the glyceride was recovered. As a result of testing the glyceride composition using Iyatroscan (Yatron), although 8% diglyceride was contained in the product of the first reaction cycle, the content of partially esterified glycerides in the glycerides of the second reaction cycle and thereafter was 1% or less. The fatty acid composition of the glyceride fractions of the 2nd to 4th reaction cycles was 45.1% caprylic acid and 54.9% palmitic acid.

Transesterification was repeated using the glyceride fractions of the 2nd to 4th reaction cycles as a starting material in order to enhance the exchange rate of caprylic acid. 3.5 g of the prepared glyceride and 7 g of caprylic acid were added to the Lipozyme IM60 (1.2 g) used in the above-mentioned reaction after which the reaction was carried out while shaking for 48 hours at 30° C. (5th cycle). After reaction, the reaction mixture was replaced with a fresh substrate mixture and the reaction was again carried out under the same conditions (6th cycle). The glyceride fractions were recovered from the 5th and 6th reaction mixtures by hexane extraction (total 4.8 g). The fatty acid composition of the resulting glyceride fraction (mol %) was 64.2% caprylic acid and 35.8% palmitic acid. The partially esterified glycerides contained in this glyceride fraction 8P8 accounted for 1% or less, and as a result of analyzing with an ODS column (Wakosil-II 3C18, 4.6×150 mm, two columns) using acetone/acetonitrile (1:1, vol/vol) for the elution solvent, the purity of 8P8 was determined to be 93%.

Transesterification was again carried out (7th cycle) for 48 hours at 30° C. using the resulting 8P8 (3.5 g) and 7 g of arachidonic acid (purity: 90%) as starting materials with the Lipozyme IM60 used in the above-mentioned reactions. After reaction, the reaction mixture was extracted with hexane under alkaline conditions to obtain a glyceride fraction (4.8 g). When the fatty acid composition of the glyceride fraction was analyzed, the contents of caprylic acid, palmitic acid, γ-linolenic acid and arachidonic acid were 38.5, 23.1, 2.4 and 34.0 mol %, respectively. As a result of fractionating this glyceride by high-performance liquid chromatography using acetone/acetonitrile (1:1, vol/vol) for the elution solvent and an ODS column (SH-345-5, 20×500 mm, YMC), the amounts of 8PA and APA were 0.72 and 0.44 g, respectively.

Example 2

8P8 was prepared by carrying out the reaction on a scale 100 times larger than the method described in Example 1, and used as a starting material.

*Rhizopus delemar* lipase (Tanabe Pharmaceutical, Talipase) was immobilized a ceramic carrier (SM-10, NGK) in accordance with the method described in J. Ferment. Bioeng., 81, 299–303 (1996). After filling a column with 10 g of the immobilized enzyme (31,000 U/g), 100 ml of a 1:2 (wt/wt) mixture of hydrated soy bean oil and caprylic acid was allowed to flow at a flow rate of 3 ml/hr at 300 C to activate the immobilized enzyme.

Next, 50 ml of soy bean oil free of water was allowed to flow and after removing the excess water, a 1:4 (wt/wt) mixture of 8P8 and arachidonic acid ethyl ester (purity: 90%) was subjected to transesterification while allowing to flow under the same conditions. 100 g of reaction mixture was distilled under a high vacuum, and after collecting the glyceride fraction as residue, it was extracted with hexane under alkaline conditions in accordance with Example 1. The solvent was then removed with an evaporator to obtain 35.7 g of hexane extract. When the composition ratio of triglyceride and fatty acid ester contained in this hexane extract was analyzed with the Iyatroscan, the ratio was found to be 91:9. In addition, as a result of analyzing the fatty acid composition, the contents of caprylic acid, palmitic acid, γ-linolenic acid, dihomo-γ-linolenic acid and arachidonic acid were 24.4, 34.5, 1.5, 2.6 and 37.0 mol %, respectively.

Example 3

In order to remove the excess water contained in the *Rhizomucor miehei* immobilized lipase (Novo Nordisk, Lipozyme IM60) used in Example 1, 100 ml of a reaction mixture comprising 12 g of said immobilized enzyme and 60 g of SUNTGA-25 (Suntory) was placed in a screw-cap vial and allowed to react while shaking for 48 hours at 30° C. (1st cycle). After leaving only the immobilized enzyme, adding the 8P8 (12 g) prepared in Example 2 and 48 g of Mead acid ethyl ester (purity: 90%), and completely replacing the upper space in the vial with nitrogen, transesterification was performed twice while shaking for 72 hours at 30° C. (2nd and 3rd cycles).

After reaction, the reaction mixtures from the 2nd and 3rd cycles were combined and 100 g of the combined reaction mixture used in the same manner as Example 2 to recover the glyceride fraction as residue after distilling under high vacuum. Next, after extracting with hexane under alkaline conditions in accordance with Example 1, the hexane was removed with an evaporator to obtain 24.1 g of glyceride fraction. When the composition ratio of triglyceride and fatty acid ester contained in this fraction was analyzed by Iyatroscan, the ratio was found to be 92:8. When the contents of fatty acid ester and each triglyceride were quantified from the peak area of a differential refractometer by performing high-performance liquid chromatography in accordance with Example 1, the MPM content was determined to be 12.0%.

The fatty acid composition of this fraction comprised caprylic acid, palmitic acid and Mead acid at 31.2, 35.7 and 33.1 mol %, respectively.

The resulting transesterified triglyceride was additionally transesterified with Mead acid ethyl ester to enhance the ester exchange rate. 12 g of transesterified triglyceride and 48 g of Mead acid ethyl ester were added to the above-mentioned immobilized enzyme and reacted while shaking for 72 hours at 30° C. (4th cycle). After reaction, 55 g of reaction mixture was distilled using the method described above to obtain 12.3 g of glyceride fraction. The fatty acid composition of this fraction comprised caprylic acid, palmitic acid and Mead acid at 5.2, 38.6 and 56.1 mol %, respectively.

Example 4

In order to remove the excess water contained in the Rhizomucor miehei immobilized lipase (Novo Nordisk, Lipozyme IM60) used in Example 1, a reaction mixture comprising 2 g of said immobilized enzyme and 10 g of SUNTGA-25 (Suntory) was placed in a 20 ml screw-cap vial and reacted while shaking for 48 hours at 30° C. (lst cycle). While leaving only the immobilized enzyme in the reaction vessel, 8P8 (12 g) prepared in Example 2 and 8 g of fatty acid mixture obtained by hydrolyzing SUNTGA-25 were added, followed by completely replacing with nitrogen and transesterification while shaking for 48 hours at 30° C. (2nd–5th cycles). After reaction, glycerides extracted with hexane from the reaction mixtures of the 2nd through 5th cycles were combined and used as a substrate for additional transesterification. 2 g of transesterified triglyceride and 10 g of fatty acid mixture derived from SUNTGA-25 were added to the reaction vessel containing the above-mentioned immobilized enzyme and reacted while shaking for 48 hours at 30° C. (6th and 7th cycles). The glyceride fractions were extracted from the reaction mixtures of the 6th and 7th cycles followed by reacting in a similar manner again using these as transesterification substrate (8th cycle). The fatty acid composition of triglyceride obtained by repeating transesterification three times as well as fatty acid composition at triglyceride positions 1 and 3 and at position 2 were analyzed. Those results are shown in Table 1.

TABLE 1

| Types of Fatty Acids | Novel Structured Lipids (units: mol %) | | |
|---|---|---|---|
| | Overall | Positions 1, 3 | Position 2 |
| 8:0 | 9 | 9 | 2 |
| 16:0 | 34 | 6 | 96 |
| 18:1 (n-9) | 11 | 16 | 0 |
| 18:2 (n-6) | 15 | 22 | 1 |
| 18:3 (n-6) | 2 | 3 | 1 |
| 20:3 (n-6) | 1 | 3 | 0 |
| 20:4 (n-6) | 15 | 23 | 0 |

Example 5

The proportion of APA in all triglycerides in human breast milk was analyzed by high-performance liquid chromatography using the APA obtained in Example 1 for a standard. An evaporating light scattering detector (DDL31, EUROSEP Instruments) was used as a detector along with an ODS column (Cosmosil, 4.6×250 mm, Nakaraitesk), and a gradient from acetone/acetonitrile (1:1, vol/vol) to 100% acetone was used for as an eluent. As a result, the proportion of APA in all triglycerides in human breast milk was confirmed to be 0.1 to 0.6 wt %. Based on the content of arachidonic acid in human breast milk (approximately 0.5 to 1.0% based on the weight ratio in oils or fats of human breast milk), 10 to 50% of arachidonic acid in human breast milk was considered to be present as APA.

Example 6

A formula was prepared that contained human breast milk type triglyceride by mixing 0.3 g of novel structured lipid obtained in Example 1 (APA or 8PA) into 100 g of powdered milk. The proportion of arachidonic acid to total fatty acid in this formula was 0.8% in the case of mixing in APA and 0.4% in the case of mixing in 8PA.

Example 7

400 g of the present triglyceride preparation prepared in large volume according to the same procedure as Example 4 and purified, 48 g of purified egg yolk lecithin, 20 g of oleic acid, 100 g of concentrated glycerin and 40 ml of 0.1 N sodium hydroxide were dispersed with a homogenizer, and distilled water for injection was added to the homogenate to bring to a total liquid volume of 4 liters. This was emulsified with a high-pressure spraying emulsifier to prepare a lipid emulsion. After filling 200 ml aliquots of said lipid emulsion into plastic bags, the plastic bags were sterilized using high-pressure steam for 20 minutes at 121° C. to obtain a lipid transfusion agent.

Example 8

The triglyceride preparation obtained in Example 3 was formulated in a form of an emulsified injection preparation in accordance with routine methods. The content of the triglyceride preparation in the emulsified injection preparation was 10% (W/V). 1.2% (W/V) of egg yolk lecithin was added as emulsifier, and osmotic pressure was adjusted with glycerin so as to be isotonic with blood.

Example 9

Male newborn pigs (body weight >1 kg) were randomly assigned to four groups of 6 animals (and siblings were assigned to different groups). All groups were raised on formula. The four groups consisted of a group in which arachidonic acid-containing triglyceride was not added to the formula (formula group), a group in which SUNTGA-25 (Suntory) was added to the formula as arachidonic acid-containing triglyceride at a concentration of 1 g/liter (SUN group), a group in which the APA obtained by the method of Example 1 was added to the formula at a concentration of 0.4 g/liter (APA group), and a group in which the 8PA obtained by the method of Example 1 was added to the formula at a concentration of 0.82 g/liter (8PA group). The SUN, APA and 8PA groups were adjusted so that the amount of arachidonic acid in the formula was roughly equal. Table 2 indicates the composition of all fatty acids of SUNTGA-25 (abbreviated as SUN in the table), APA and 8PA along with the composition of fatty acids at triglyceride position 2.

TABLE 2

| Fatty Acid | Total Fatty Acids | | | Fatty Acids at Position 2 | | |
|---|---|---|---|---|---|---|
| | SUN | APA | 8PA | SUN | APA | 8PA |
| 8:0 | 0 | 0 | 33.3 | 0 | 0 | 0 |
| 14:0 | 0.4 | 0 | 0 | 0 | 0 | 0 |
| 16:0 | 15.0 | 33.3 | 33.3 | 0.9 | 100.0 | 100.0 |
| 18:0 | 6.4 | 0 | 0 | 0 | 0 | 0 |
| 18:1 n-9 | 14.3 | 0 | 0 | 12.4 | 0 | 0 |

TABLE 2-continued

| Fatty | Total Fatty Acids | | | Fatty Acids at Position 2 | | |
|---|---|---|---|---|---|---|
| Acid | SUN | APA | 8PA | SUN | APA | 8PA |
| 18:2 n-6 | 25.1 | 0 | 0 | 36.0 | 0 | 0 |
| 18:3 n-6 | 2.2 | 0 | 0 | 2.7 | 0 | 0 |
| 20:0 | 0.5 | 0 | 0 | 0.5 | 0 | 0 |
| 20:3 n-6 | 3.1 | 0 | 0 | 3.6 | 0 | 0 |
| 20:4 n-6 | 27.1 | 66.7 | 33.4 | 36.5 | 0 | 0 |
| 22:0 | 2.0 | 0 | 0 | 1.3 | 0 | 0 |
| 24:0 | 3.9 | 0 | 0 | 6.1 | 0 | 0 |

Fatty acids are indicated as (number of carbon atoms: number of double bonds) and are represented as: 16:0 palmitic acid, 18:0 stearic acid, 18:1 n-9 oleic acid, 18:2 n-6 linoleic acid, 18:3 n-6 γ-linolenic acid, 20:3 n-6 dihomo-γ-linolenic acid, 20:4 n-6 arachidonic acid.

After fasting the animals for 10 to 12 hours, on the 18th day of dosing, blood samples were collected, and the liver and lungs were excised (and stored at −80° C. until analysis). The fatty acid compositions of plasma and liver were affected by fatty acids present in the formulas and when the formula groups were compared, although the arachidonic acid contents of the SUN, APA and 8PA groups were higher, there were no significant differences observed between these groups with respect to arachidonic acid content. This is believed to be because the tissues used were directly affected by dietary fatty acids. Therefore, the fatty acid composition of phospholipid in the lungs was analyzed. Those results are shown in Table 3.

TABLE 3

| Fatty | Fatty Acid Composition of Lung Phospholipid | | | |
|---|---|---|---|---|
| Acid | Formula Group | SUN Group | APA Group | 8PA Group |
| 16:0 | 31.0 ± 0.5 | 29.2 ± 0.3 | 30.3 ± 0.4 | 32.7 ± 0.5 |
| 18:0 | 13.4 ± 0.2 | 13.2 ± 0.3 | 11.6 ± 0.5 | 12.5 ± 0.4 |
| 18:1 n-9 | 23.7 ± 0.5 | 23.0 ± 0.2 | 22.8 ± 0.4 | 23.1 ± 0.3 |
| 18:2 n-6 | 12.1 ± 0.3 | 12.7 ± 0.2 | 12.4 ± 0.3 | 12.6 ± 0.2 |
| 20:4 n-6 | 8.1 ± 0.2 | 9.1 ± 0.1 | 10.5 ± 0.3 | 10.2 ± 0.2 |
| 22:5 n-3 | 2.2 ± 0.1 | 2.1 ± 0.1 | 2.4 ± 0.2 | 1.9 ± 0.1 |
| 22:6 n-3 | 0.8 ± 0.1 | 0.7 ± 0.1 | 0.8 ± 0.1 | 0.8 ± 0.1 |

There were no significant differences in the proportions of arachidonic acid in the fatty acid composition of lung phospholipid. The proportion of arachidonic acid among lung phospholipids in the SUN group can be predicted to be higher than in the formula group. However, despite containing the same amount of arachidonic acid, the proportions of arachidonic acid among lung phospholipids in the APA and 8PA groups were significantly higher than in the SUN group. This result is considered to be due to the positional characteristics of the structured lipid triglyceride of the present invention.

What is claimed is:

1. A triglyceride represented by the following general formula (I):

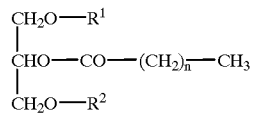

wherein $R^1$ and $R^2$ are acyl groups, which may be oxidised, of unsaturated fatty acids having from 18 to 22 carbon atoms, n represents an integer from 14 to 16, at least one of $R^1$ and $R^2$ is ω6-, ω9-, or ω3-unsaturated fatty acid, but excluding those triglycerides in which (i) when n is 14:
$R^1$ and $R^2$ are both eicosapentaenoate:
$R^1$ and $R^2$ are both docosahexaenoate:
$R^1$ and $R^2$ are both linolenate:
$R^1$ is linoleate and $R^2$ is linolenate:
$R^1$ is eicosapentaenoate and $R^2$ is docosahexaenoate:
(ii) when n is 16, $R^1$ is docosahexaenoate and $R^2$ is docosahexaenoate or 22:5 ω3.

2. A triglyceride according to claim 1, wherein the acyl group of $R^1$ and the acyl group of $R^2$ are different.

3. A triglyceride represented by the following general formula (II):

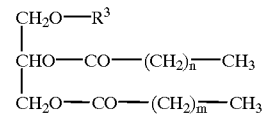

wherein $R^3$ represents an acyl group, which may be oxidised, of ω6-, ω9- or ω3-unsaturated fatty acid having from 18 to 22 carbon atoms, n represents an integer from 14 to 16, and m represents an integer from 2 to 16, but excluding those triglycerides in which (i) when n and m are both 14, $R^3$ is eicosapentaenoate, linolenate or linoleate;
(ii) when n and m are both 16, $R^3$ is linoleate.

4. A triglyceride as set forth in claim 1, wherein the oxidized acyl group is a hydroxylated, epoxidated or hydroxyepoxidated acyl group.

5. A triglyceride as set forth in claim 1, wherein the unsaturated fatty acid having 18 to 22 carbon atoms is an unsaturated fatty acid selected from the group consisting of:

9,12-octadecadienoic acid (linoleic acid) 18:2, ω6
6,9,12-octadecatrienoic acid (γ-linolenic acid) 18:3, ω6
8,11,14-eicosatrienoic acid (dihomo-γ-linolenic acid) 20:3 ω6
5,8,11,14-eicosatetraenoic acid (arachidonic acid) 20:4, ω6
7,10,13,16-docosatetraenoic acid 22:4, ω6
4,7,10,13,16-docosapentaenoic acid 22:5, ω6
6,9-octadecadienoic acid 18:2, ω9
8,11-eicosadienoic acid 20:2, ω9
5,8,11-eicosatrienoic acid (Mead acid) 20:3, ω9
9,12,15-octadecatrienoic acid (α-linolenic acid) 18:3, ω3
6,9,12,15-octadecatetraenoic acid (stearidonic acid) 18:4, ω3
11,14,17-eicosatrienoic acid (dihomo-α-linolenic acid) 20:3, ω3
8,11,14,17-eicosatetraenoic acid 20:4, ω3
5,8,11,14,17-eicosapentaenoic acid 20:5, ω3
7,10,13,16,19-docosapentaenoic acid 22:5, ω3, and
4,7,10,13,16,19-docosahexaenoic acid 22:6, ω3.

6. A triglyceride as set forth in claim 1, selected from the group consisting of the following triglycerides:

1,3-diarachidonyl-2-palmitoyl triglyceride,
1-arachidonyl-3-docosahexaenoyl-2-palmitoyl triglyceride,
1-arachidonyl-3-octanoyl-2-palmitoyl triglyceride,
1-(dihomo-γ-linolenyl)-3-docosahexaenoyl-2-palmitoyl triglyceride, 1-docosahexaenoyl-3-octanoyl-2-palmitoyl triglyceride,
1-arachidonyl-3-(dihomo-γ-linolenyl)-2-palmitoyl triglyceride,
1-(dihomo-γ-linolenyl)-3-octanoyl-2-palmitoyl triglyceride,
1,3-bis(dihomo-γ-linolenyl)-2-palmitoyl triglyceride,
1,3-bis(5,8,11-eicosatrienoyl)-2-palmitoyl triglyceride,
1-(5,8,11-eicosatrienoyl)-3-octanoyl-2-palmitoyl triglyceride,
1-arachidonyl-3-(5,8,11-eicosatrienoyl)-2-palmitoyl triglyceride, and
1-docosahexaenoyl-3-(5,8,11-eicosatrienoyl)-2-palmitoyl triglyceride.

7. A food composition containing a triglyceride as set forth in claim 1 according to special nutritional requirements.

8. A food composition as set forth in claim 7, wherein said food composition is a functional food, nutritional supplement food, premature infant formula, infant formula, baby food, pregnancy food or elderly food.

9. An animal feed containing a triglyceride as set forth in claim 1.

10. A therapeutic nutritional product containing at least one type of triglyceride as set forth in claim 1 and a neutral carrier suitable for oral, intraintestinal or parenteral administration depending on the case.

11. A pharmaceutical composition containing at least one type of triglyceride as set forth in claim 1.

12. An analytical standard reagent comprising a triglyceride as set forth in claim 1.

13. A triglyceride as set forth in claim 3, wherein the oxidized acyl group is a hydroxylated epoxidated or hydroxyepoxidated acyl group.

14. A triglyceride as set forth in claim 3, wherein the unsaturated fatty acid having 18 to 22 carbon atoms is an unsaturated fatty acid selected from the group consisting of:

9,12-octadecadienoic acid (linoleic acid) 18:2,
6,9,12-octadecatrienoic acid (γ-linolenic acid) 18:3,
8,11,14-eicosatrienoic acid (dihomo-γ-linolenic acid) 20:3,
5,8,11,14-eicosatetraenoic acid (arachidonic acid) 20:4,
7,10,13,16-docosatetraenoic acid 22:4,
4,7,10,13,16-docosapentaenoic acid 22:5,
6,9-octadecadienoic acid 18:2,
8,11-eicosadienoic acid 20:2,
5,8,11 -eicosatrienoic acid (Mead acid) 20:3,
9,12,15-octadecatrienoic acid (α-linolenic acid) 18:3,
6,9,12,15-octadecatetraenoic acid (stearidonic acid) 18:4,
11,14,17-eicosatrienoic acid (dihomo-α-linolenic acid) 20:3,
8,11,14,17-eicosatetraenoic acid 20:4,
5,8,11,14,17-eicosapentaenoic acid 20:5,
7,10,13,16,19-docosapentaenoic acid 22:5, and
4,7,10,13,16,19-docosahexaenoic acid 22:6.

15. A triglyceride as set forth in claim 3, selected from the group consisting of the following triglycerides:

1,3-diarachidonyl-2-palmitoyl triglyceride,
1-arachidonyl-3-docosahexaenoyl-2-palmitoyl triglyceride,
1-arachidonyl-3-octanoyl-2-palmitoyl triglyceride,
1,3-didocosahexaenoyl-2-palmitoyl triglyceride,
1-(dihomo-γ-linolenyl)-3-docosahexaenoyl-2-palmitoyl triglyceride,
1-docosahexaenoyl-3-oxtanoyl-2-palmitoyl triglyceride,
1-arachidonyl-3-(dihomo-γ-linolenyl)-2-palmitoyl triglyceride,
1-(dihomo-γ-linolenyl)-3-octanoyl-2-palmitoyl- triglyceride,
1,3-bis(dihomo-γ-linolenyl)-2-palmitoyl triglyceride,
1,3-bis(5,8,11-eicosatrienoyl)-2-palmitoyl triglyceride,
1-(5,8,11-eicosatrienoyl)-2-palmitoyl triglyceride,
1-arachidonyl-3-(5,8,11-eicosatrienoyl)-2-palmitoyl triglyceride, and
1-docosahexaenoyl-3-(5,8,11-eicosatrienoyl)-2-palmitoyl triglyceride.

16. A food composition containing a triglyceride as set forth in claim 3 according to special nutritional requirements.

17. A food composition as set forth in claim 16, wherein said food composition is a functional food, nutritional supplement food, premature infant formula, infant formula, baby food, pregnancy food or elderly food.

18. An animal feed containing a triglyceride as set forth in claim 3.

19. A therapeutic nutritional product containing at least one type of triglyceride as set forth in claim 3 and a neutral carrier suitable for oral, intraintestinal or parenteral administration depending on the case.

20. A pharmaceutical composition containing at least one type of triglyceride as set forth in claim 3.

21. An analytical standard reagent comprising a triglyceride as set forth in claim 3.

22. A triglyceride represented by the following general formula (I):

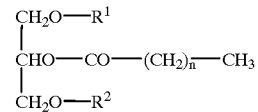

wherein $R^1$ and $R^2$ are acyl groups, which may be oxidised, of unsaturated fatty acids having from 18 to 22 carbon atoms, n represents an integer from 14 to 16, at least one of $R^1$ and $R^2$ is selected from the group consisting of:

8,11,14-eicosatrienoic acid (dihomo-γ-linolenic acid) 20:3, ω6
5,8,11,14-eicosatetraenoic acid (arachidonic acid) 20:4, ω6
7,10,13,16-docosatetraenoic acid 22:4, ω6
6,9-octadecadienoic acid 18:2, ω9
8,11-eicosadienoic acid 20:2, ω9
5,8,11-eicosatrienoic acid (Mead acid) 20:3, ω9
9,12,15-octadecatrienoic acid (α-linolenic acid) 18:3, ω3
6,9,12,15-octadecatetraenoic acid (stearidonic acid) 18:4, ω3
11,14,17-eicosatrienoic acid (dihomo-α-linolenic acid) 20:3, ω3
8,11,14,17-eicosatetraenoic acid 20:4, ω3
5,8,11,14,17-eicosapentaenoic acid 20:5, ω3 and
7,10,13,16,19-docosapentaenoic acid 22:5, ω3.

* * * * *